United States Patent [19]  
Deli et al.

[11] 3,980,464  
[45] Sept. 14, 1976

[54] CONTROL OF WEEDS WITH 5-PROPIONYLAMINO-3-METHYLISOTHIAZOLE

[75] Inventors: Joseph Deli, Rockford, Ill.; Henry C. Stevens, Akron, Ohio

[73] Assignee: PPG Industries, Inc., Pittsburgh, Pa.

[22] Filed: May 5, 1975

[21] Appl. No.: 574,791

[52] U.S. Cl. .............................. 71/90; 260/306.8 A
[51] Int. Cl.² ............................................ A01N 9/22
[58] Field of Search ............................................ 71/90

[56] References Cited
UNITED STATES PATENTS

| | | | |
|---|---|---|---|
| 3,515,538 | 6/1970 | Jeno et al. | 71/90 |
| 3,847,588 | 11/1974 | Pilgrim et al. | 71/90 |
| 3,890,131 | 6/1975 | Buttimore | 71/90 |

*Primary Examiner*—Lewis Gotts
*Assistant Examiner*—Catherine L. Mills
*Attorney, Agent, or Firm*—Robert J. Grassi

[57] ABSTRACT

Weeds, particularly broadleaf weeds, are controlled by contacting them with a lethal dosage of 5-propionylamino-3-methylisothiazole.

13 Claims, No Drawings

CONTROL OF WEEDS WITH 5-PROPIONYLAMINO-3-METHYLISOTHIAZOLE

CROSS REFERENCE TO RELATED APPLICATIONS

This application is related to the subject matter of assignee's other applications, N-(3-methyl-5-isothiazolyl)-2-methylpentanamide, Ser. No. 574,792, filed even date herewith.

BACKGROUND OF THE INVENTION

1. Field of the Invention

The invention relates to the herbicidal use of 5-propionylamino-3-methylisothiazole against weeds, primarily, broadleaf weeds 2. Description of the Prior Art Robba and Moreau, in *Annales pharmaceutique francaises*, 22, 1964, No. 3, pages 201–210, describe 5-propionylamino-3-methylisothiazole as a derivative formed from 5-amino-3-methylisothiazole, (a compound described by Adam et al in U.S. Pat. No. 2,871,243) and propionyl chloride, which they nitrated at the 4 position of the isothiazole ring, to form the derivative 5-propionylamino-4-nitro-3-methylisothiazole. This derivative was inactive against *Trichononos vaginalis*, a pathogen causing infections of the human vagina. Stock et al, in U.S. 2,871,243, describe the starting material, 5-amino-3-methylisothiazole, as an intermediate to the derivative 5-(p-acetamidobenzenesulphonylamino)-3-methylisothiazole, a useful bactericide for *Escherichia coli*. Other workers, in the Journal of the Chemical Society, 1959, pages 3061 to 3071, describe the acetyl, dichloroacetyl and benzoyl derivatives of the 3-amino-5-methylisothiazole but give no uses for them. The chloroacetyl derivative, an analgesic, is listed in Volume 59 of *Chemical Abstracts*, Column 2791 (1963). Stock et al, in U.S. 3,186,999, describe semi-carbazone, and thiocarbazone derivatives of 5-amino-3-methylisothiazole, which are active against pox viruses. In Japanese patent 5641/64, S. Kamio et al (Chemical Abstract 59, column 2791a) describe monohalogenocarboxylic amides of isothiazole as useful intermediates for amino-carboxylic acid derivatives.

Others describe certain specified cyanated, halogenated, benzoated, or urea-substituted isothiazole derivatives as herbicides for certain weeds or fungicides for certain fungi in U.S. Pat. Nos. 3,155,678, 3,393,992, 3,454,591, 3,541,108, 3,564,985, 3,622,593, and 3,692,795. None of the above-mentioned references describe or suggest that a simple acylamino derivative of 3-methylisothiazole, such as 5-propionylamino-3-methylisothiazole, has herbicidal usage particularly against broadleaf weeds.

SUMMARY OF THE INVENTION

In accordance with this invention, 5-propionylamino-3-methylisothiazole is employed to control weeds, notably broadleaf weeds. This control is achieved by use of a herbicidal amount of the compound, either alone or formulated into a suitable agricultural composition. Preferably, the foliage of the weed (after emergence of the weed) is contacted with the compound, although the compound can be used with good effect in pre-emergent treatments. Broadleaf weed species in particular are especially well controlled by the compound.

DESCRIPTION OF THE PREFERRED EMBODIMENTS

Weeds, primarily broadleaf weed species, are effectively controlled according to this invention by the use of 5-propionylamino-3-methylisothiazole, usually by contacting the weeds with a herbicidal amount of the compound. The control can be by application of the compound to the soil or weed (e.g. the weed environment) either prior to or after emergence of the weed, or in any combination thereof, but the preferred method is to contact the weed after emergence of the weeds, that is when the weeds protrude from the soil. If both crop plants and weeds are emerging, then the compound is applied after emergence of both. A preferred method is to contact the foliage of the weed with a lethal dosage of the compound. This is readily achieved by applying the compound itself or in the form of a suitable agricultural composition to the foliage of the weed. The lethal (herbicidal) dosage will of course vary with the plant size, weather, soil and the crop planted. A workable lethal dosage for plant contact is from 0.25 to 500 lbs. per acre (0.27 to 550 kilogram/hectare) of the compound whether applied itself or in the form of an agricultural composition, while from 0.25 to 50 lbs. per acre (0.27 to 55 kilograms per hectare) is normally the range to use under various climatic conditions, but preferably from 1 to 10 lbs. per acre (1.1 to 11 kilogram/hectare) under optimum conditions.

It has been discovered that the compound 5-propionylamino-3-methylisothiazole is particularly effective against broadleaf weeds, particularly those of the genera: Chenopodium, Amaranthus, Abutilon, Datura, Ipomoea, Sida, Sesbania, Xanthium, and Cassia. The compounds were found extremely effective against the broadleaf species: *Chenopodium album* (common lambsquarter), *Amaranthus retroflexus* (redroot pigweed), *Datura stramonium* (jimsonweed), *Ipomoea purpurea* (tall morningglory), *Ipomoea hederocea* (ivyleaf morningglory), *Sida spinosa* (teaweed, prickly sida), *Abutilon theophrasti* (velvetleaf), *Sesbania spp.* (Coffeeweed), *Xanthium pensylvanicum* (common cocklebur), and *Cassia obtusifolia* (sicklepod).

The following Examples illustrate the manner in which this invention may be practiced.

EXAMPLE 1

The effectiveness of 5-propionylamino-3-methylisothiazole as a herbicide for controlling broadleaf weeds under field conditions is illustrated in this Example.

Six 60-foot rows of *Gylcine max*, soybeans seeds, (variety: Amsoy) and six 60-foot rows of *Gossypium hirsutum*, cotton seed, (variety: Coker 201) were planted on a farm, in Barberton, Ohio, on Aug. 28, 1973. One week later a mixture of weed seeds was evenly distributed over the crop rows in an 8 to 10 inch band, covered lightly with soil, and watered.

The mixture of weed seeds was a representative cross-section of broadleaf weeds, and contained, in about equal weight, seeds of a species of each of the following genera: Chenopodium, Amaranthus, Abutilon, Datura, Ipomoea, Sida, Sesbania, Xanthium, and Cassia. The particular weed species used were: *Chenopodium album* (common lambsquarter), *Amaranthus retroflexus* (redroot pigweed), *Datura stramonium* (jimsonweed), *Ipomoea purpurea* (tall morningglory), *Ipomoea hederacea* (ivyleaf morning glory), *Sida*

*sponosa* (teaweed, prickly sida), *Abutilon theophrasti* (velvetleaf), *Sesbania spp.* (coffeeweed), *Xanthium pensylvanicum* (common cocklebur), and *Cassia obtusifolia* (sicklepod).

Approximately four weeks after the weed seeds were planted, when the soybean and cotton plants were approximately 5–6" and 4–5" tall respectively, and the weeds were from 1 inch to 4 inches in height, the weeds were contacted with the compound 5-propionylamino-3-methylisothiazole.

This contact was achieved by applying the compound as a directed postemergence spray, that is a spray directed on weeds below the crop foliage. The band width of the spray was approximately 12 inches wide, and the row length to which it was applied was about 20 feet. This row length was followed by an untreated band of 20 feet which was followed by another treated band. The volume of spray per 20 sq. ft. area (20 ft. long by 1 ft. wide) was 87 ml., which is equivalent to 50 gallons per acre. The amount of the 5-propionylamine-3-methylisothiazole per 87 ml. was adjusted to give application rates of 0.5, 0.10, 2.0 lbs. per acre (0.55, 1.1, 2.2 kilograms/hectare) of the compound itself. The solvent used was water which contained 0.5 vol. %/vol. of Tween 20, a surfactant.

The plots were observed at regular intervals, and two weeks after application, a weed control rating was taken on a 0-10 scale; zero ("0") no control, that is no plants were killed and ten ("10") complete control, all plants were killed.

The average value of the control rating based on two replicates showed that at 0.5 lb./acre (0.55 kilograms/hectare) most weeds were completely killed, except *Amaranthus retroflexus* (redroot pigweed) which had about 70% of the plants killed, *Ipomoea purpurea* (tall morningglory) and *Ipomoea hederacea* (ivyleaf morningglory) which had about 90% of the plants killed, and *Xanthium pensylvanicum* (cocklebur) which had about 80% of the plants killed.

At an application rate of 1 lb./acre (1.1 kilograms/hectare), about 80% of the *Amaranthus retroflexus* and *Xanthium pensylvanicum* were killed, and 100% of the *Ipomoea purpurea* and the *Ipomoea hederacea* were killed while, as before, all other weeds were completely killed.

At an application rate of 2.0 lb./acre (2.2 kilograms/hectare), all weeds were killed.

These field test results show the compound's herbicidal activity against weeds and, in particular, broadleaf weeds. Although the lethal dosage shown was for 0.5 to 2.0 lbs./acre (0.55 to 2.2 kilograms/hectare), such a dosage can be varied from 0.25 to 500 lbs./acre (0.27 to 550 kilograms/hectare), depending upon the type and the amount of weeds and the weather, but generally 0.25 to 50 lbs./acre will suffice, and under optimum conditions from 0.25 to 10 lbs./acre is preferred.

It is to be noted, that weed species of the *Gossypium* genus are also effectively controlled by the compound.

The compound 3-amino-5-methylisothiazole, itself, and the compound 3-acetylamino-5-methylisothiazole, and 3-benzamido-5-methylisothiazole when tested under comparable conditions against broadleaf leaf weeds and grassy weeds had no activity, in comparison to the high activity of 3-propionylamino-5-methylisothiazole.

The compound, 5-propionylamino-3-methylisothiazole, is readily made by reacting propionyl chloride with 5-amino-3-methylisothiazole in the manner described by M. Robba and R. C. Moreau (*Annales pharmaceutique francaises*, 22, 1964 No. 3, pages 201–210.

The compound can also be made by reacting 5-amino-3-methylisothiazole with propionic anhydride, as illustrated by the following example.

EXAMPLE 2

A 40 gram quantity (0.265 mole) of 5-amino-3-methylisothiazole hydrochloride was neutralized with 270 ml. of aqueous NaOH and the resulting mixture extracted with three 100 ml. portions of ethyl ether. The extracts were combined, dried with anhydrous $MgSO_4$, filtered and evaporated under reduced pressure to afford 32 grams of the free amine as a brown oil.

The free amine was placed into a 250 ml. three-neck flask equipped with a stirrer, thermometer and reflux condenser. To it was added a 103.4 gram quantity (0.795 mole) of propionic anhydride. Upon mixing, the heat given off during reaction warmed the mixture to 80°C. and then it was heated to 100°C. and maintained at that temperature for 2 hours, prior to cooling to ambient temperature. During the cooling period, product material crystallized out of solution and a slurry formed. The crystalline slurry was then filtered, and formed into pulp with 100 ml. of petroleum-ether, and the pulp was air dried to form 22.8 grams of the desired product material (22.8 gram); it had a melting point of 167°–170°C.

A second crystal crop was obtained by pouring the original filtrate into 250 ml. of petroleum-ether followed by filtration of the precipitated crystals to afford an additional 13.8 grams of an off-white product material having the same melting point. The total weight of the product obtained was 36.6 grams, (81% yield).

Normally, use of 5-propionylamino-3-methylisothiazole is by way of an appropriate formulation. For example, it may be formulated as a granule of relatively large size, as a powdery dust, as a wettable powder, as an emulsifiable concentrate, as a solution, etc., depending upon the mode of application desired. For preemergence application to control vegetation, the compound is usually applied to the area as a spray, dust, or granule; for postemergence control of an established weed, a spray or dust is generally employed. In all these formulations, the active ingredient is diluted with an inert carrier, either a solid or liquid diluent. The formulations may contain as little as 0.1 percent or as much as 99 percent or more by weight of the active ingredient.

Dusts are mixtures of the active compound with finely divided solids such as talc, altapulgite, clay, kieselguhr, and other organic and inorganic solids which act as dispersants and carriers for the compound. The finely divided solids have an average particle size of less than about 50 microns. A typical dust formulation will contain from 1.0 to 10.0 parts by weight of 5-propionylamino-3-methylisothiazole to 99.0 to 90.0 parts by weight of talc.

Wettable powders for preemergent or postemergent application are finely divided solid particles, which disperse readily in water or other liquids. The wettable powder is applied to the soil, seed or plant as a dry dust or as a water or other liquid emulsion.

Typical wettable powder carriers are Fuller's earth, Kaolin clays, silicas, and other highly absorbent, readily wet, inorganic diluents. Wettable powders normally contain about 5 to 80 weight percent of the active ingredient, depending on the absorbency of the carrier, and usually contain a small amount of a wetting, dispersing, or emulsifying agent to facilitate dispersion.

For example, a useful wettable powder formulation comprises by weight about 80.8 parts of 5-propionylamino-3-methylisothiazole, 17.9 parts of Palmetho clay and 1.0 part of sodium lignosulfate and 0.3 parts of sulfonated aliphatic polyester as wetting agents.

Other postemergent formulations are emulsifiable concentrate. These are homogenous liquid or paste compositions which are dispersible in water or other liquids. They may consist entirely of 5-propionylamino-3-methylisothiazole and a liquid or solid emulsifying agent, or they may also contain a liquid carrier, such as xylene, heavy aromatic naphthas, or other non-volatile organic solvents. These emulsifiable concentrates are dispersed in a liquid carrier, e.g. water, and generally are applied as a spray to the area or plant to be treated. The weight percent of 5-propionylamino-3-methylisothiazole in these concentrates varies with the manner of application, but generally is from 0.5 to 95 percent.

Representative wetting, dispersing and emulsifying agents for the agricultural formulations are alkyl and alkaryl sulfonates and sulfates, and their alkali salts; polyethylene oxides, sulfoxided oils, fatty acid esters of polyhydric alcohols, and other surface-active agents, e.g. Tween 20, a commercial surfactant. If used, the surfactant would vary from 0.25 to 15 weight percent of the composition.

Other formulations for herbicidal applications include simple solutions of the compound in solvents in which it is completely soluble at the desired concentration, e.g. acetone or other organic solvents; aerial spray formulations comprising relatively coarse particles coated with 5-propionylamino-3-methylisothiazole, and pressurized spray formulations such as aerosols, which use low boiling dispersant solvents such as Freon. All of these formulations may be used to apply the active compound to the area to be treated.

These formulations may also include other agriculturally useful materials such as nematocides, pesticides, and herbicides which are nontoxic to the desired vegetation, but which are effective against other weeds, pests, and nematodes, their eggs, fungi and bacteria so that one application will serve to rid the area of several undesirable species. For example, 5-propionylamino-3-methylisothiazole may be used with sodium azide, or potassium azide in formulations which contain stabilizers for both the azide and the isothiazole compound. Other combinations of the compound 5-propionylamino-3-methylisothiazole are those with certain ureas, thiocarbamates, carbamates, which increase the useful herbicidal spectrum of the thiazole, reduce the number of applications required by husbandmen and others who require use of these compounds to assist the healthful growth of crops. It may be used in combination with fertilizers, particularly those used in foliage applications, provided of course that the composition formulation is such that 5-propionylamino-3-methylisothiazole is not hydrolyzed, e.g., the pH conditions are maintained between 2–10, preferably between 5 and 8.

When the compound is applied in the form of a suitable agricultural composition, the application rate of such formulation is such that the herbicidal dosage of the compound, itself, is between 0.25 to 500 pounds per acre (0.27 to 550 kilograms per hectare). Generally, the rate is from 0.25 to 50 pounds per acre (0.27 to 55 kilogram per hectare), but preferably from 1 to 10 pounds per acre (1.1 to 11 kilograms per hectare) under optimum conditions.

While the invention has been described with reference to specific details of certain illustrative embodiments, it is not intended that it shall be limited thereby except insofar as such details appear in the accompanying claims.

We claim:

1. A method of controlling weeds which comprises contacting the weed environment with a herbicidal dosage of 5-propionylamino-3-methylisothiazole.

2. The method as recited in claim 1, wherein the weed is a broad leaf weed.

3. The method as recited in claim 2, wherein the foliage of the weed is contacted with the compound.

4. The method as recited in claim 3, wherein said weed is contacted with the compound after emergence of the weed.

5. The method as recited in claim 4, wherein the weed is *Chenopodium album*.

6. The method as recited in claim 4, wherein the weed is *Amaranthus retroflexus*.

7. The method as recited in claim 4, wherein the weed is *Sida spinosa*.

8. The method as recited in claim 4, wherein the weed is *Datura stramonium*.

9. The method as recited in claim 4, wherein the weed is *Ipomoea purpurea*.

10. The method as recited in claim 4, wherein the weed is *Ipomoea hederacea*.

11. The method as recited in claim 4, wherein the weed is *Abutilon theophrasti*.

12. The method as recited in claim 4, wherein the weed is *Sesbania spp*.

13. The method as recited in claim 4, wherein the weed is *Cassia obtusfolia*.

* * * * *